United States Patent
Chen et al.

(10) Patent No.: US 12,016,874 B2
(45) Date of Patent: Jun. 25, 2024

(54) METHODS AND COMPOSITIONS FOR TREATING CARBAPENEM-RESISTANT KLEBSIELLA PNEUMONIAE INFECTIONS

(71) Applicant: City University of Hong Kong, Hong Kong (CN)

(72) Inventors: Sheng Chen, Hong Kong (CN); Bill Kwan-wai Chan, Hong Kong (CN); Hongyuhang Ni, Hong Kong (CN)

(73) Assignee: City University of Hong Kong, Hong Kong (CN)

( * ) Notice: Subject to any disclaimer, the term of this patent is extended or adjusted under 35 U.S.C. 154(b) by 0 days.

(21) Appl. No.: 17/819,970

(22) Filed: Aug. 16, 2022

(65) Prior Publication Data
US 2023/0398139 A1     Dec. 14, 2023

(30) Foreign Application Priority Data
Jun. 10, 2022  (CN) .......................... 202210655492.2

(51) Int. Cl.
| | | |
|---|---|---|
| *A61K 31/7072* | (2006.01) | |
| *A61K 31/496* | (2006.01) | |
| *A61K 45/06* | (2006.01) | |
| *A61P 31/04* | (2006.01) | |

(52) U.S. Cl.
CPC ........ *A61K 31/7072* (2013.01); *A61K 31/496* (2013.01); *A61K 45/06* (2013.01); *A61P 31/04* (2018.01)

(58) Field of Classification Search
None
See application file for complete search history.

(56) References Cited

U.S. PATENT DOCUMENTS 10,098,904 B2 * 10/2018 Coates .................... A61P 31/06

OTHER PUBLICATIONS

Diep, John K., et al. "Polymyxin B in combination with rifampin and meropenem against polymyxin B-resistant KPC-producing Klebsiella pneumoniae." Antimicrobial agents and chemotherapy 61.2 (2017): 10-1128.*
Petrosillo, Nicola, et al. "Treatment of carbapenem-resistant Klebsiella pneumoniae: the state of the art." Expert review of anti-infective therapy 11.2 (2013): 159-177.*
Kohno, Jun, et al. "Boromycin, an anti-HIV antibiotic." Bioscience, biotechnology, and biochemistry 60.6 (1996): 1036-1037.*
Gallicano, Keith D., et al. "Induction of zidovudine glucuronidation and amination pathways by rifampicin in HIV-infected patients." British journal of clinical pharmacology 48.2 (1999): 168-179.*
Shon, Alyssa S., Rajinder PS Bajwa, and Thomas A. Russo. "Hypervirulent (hypermucoviscous) Klebsiella pneumoniae: a new and dangerous breed." Virulence 4.2 (2013): 107-118.*
Antonello R M, Di Bella S, Betts J, et al. Zidovudine in synergistic combination with fosfomycin: an in vitro and in vivo evaluation against multidrug-resistant Enterobacterales[J]. International journal of antimicrobial agents, 2021, 58(1): 106362.
Antonello R M, Di Bella S, Betts J, et al. Zidovudine plus Fosfomycin: synergistic effect against clinical isolates of multidrug-resistant Enterobacterales. In vitro and in vivo evidence[C]//31st ECCMID. ESCMID, 2021: 1-1.

* cited by examiner

Primary Examiner — Patrick T Lewis
(74) Attorney, Agent, or Firm — S&F/WEHRW

(57) ABSTRACT

Methods of using rifampicin and zidovudine and pharmaceutical compositions comprising the same to inhibit growth of and/or kill *Klebsiella pneumoniae*, such as antibiotic-resistant *Klebsiella pneumoniae*.

13 Claims, 10 Drawing Sheets

METHODS AND COMPOSITIONS FOR TREATING CARBAPENEM-RESISTANT KLEBSIELLA PNEUMONIAE INFECTIONS

CROSS-REFERENCE TO RELATED APPLICATIONS

The present application claims priority from China Patent Application No. 202210655492.2, filed on 10 Jun. 2022, which is hereby incorporated by reference in its entirety.

TECHNICAL FIELD

The present disclosure relates to a pharmaceutical composition comprising rifampin and zidovudine, and a preparation method and application thereof.

BACKGROUND

Rifampicin and zidovudine are both FDA-approved drugs. Rifampicin is a potent inhibitor of *Haemophilus influenzae*, meningococcus and *Mycobacterium tuberculosis*. Zidovudine has strong activity against the HIV virus. The antibacterial activity of zidovudine was reported as early as 1987, and it is now known to have antibacterial activity against various Gram-negative bacteria of the family Enterobacteriaceae.

Currently, *Klebsiella pneumoniae* has become the second most prevalent Gram-negative bacterial pathogen, causing various infections, such as bacteremia, meningitis, purulent liver abscess (PLA), pneumonia, and abdominal cavity infection etc. These infections often threaten some patients in high-risk populations, such as patients with organ transplants, chronic liver disease, and renal insufficiency, and the like. *Klebsiella pneumoniae* has the ability to propagate rapidly through hospitals and has caused multiple outbreaks worldwide.

It has been reported that plasmids from *K. pneumoniae* encode a number of virulence factors, such as those involved in capsule formation, fimbriation, resistance serum, and siderophore-related factors. These virulence factors enable *K. pneumoniae* to escape the patient's immune system and cause a systemic fatal infection.

The emergence of multidrug-resistant *K. pneumoniae* has become a major problem worldwide. Carbapenem-resistant *K. pneumoniae* (CRKP) has been increasingly reported in China reaching 21.9% of all *K. pneumoniae* infections in hospitals according to China Antimicrobial Surveillance Network (CHINET) 2021 report. Data from this study showed a very high mortality rate caused by CRKP infections, reaching 24.2% for the 28-day crude mortality and over 45% for blood-stream infections. Antibiotic resistance in *K. pneumoniae* can be attributed to intrinsic molecular mechanisms, including expression of RND-type efflux pump system-related proteins such as acrAB, kexD, oqxAB, and eefABC, inhibition of outer membrane porin-related genes such as OmpK, as well as high expression of various hydrolases such as β-lactamase. These mechanisms have helped *K. pneumoniae* develop resistance to a series of antibiotics, including beta-lactams, fluoroquinolones, and chloramphenicol. In addition to the intrinsic mechanisms, *K. pneumoniae* can also obtain plasmids carrying resistance genes by horizontal gene transfer. For example, clinical isolates of *K. pneumoniae* carrying carbapenemase genes such as $bla_{NDM-1}$, $bla_{KPC}$ and $bla_{OXA-48}$ have been reported around the world.

The development of novel treatments for *K. pneumoniae* infections has become a very urgent objective. However, progress in antibiotic development has lagged far behind the development of bacterial resistance. At present, the main difficulties faced in the development of antibiotics include the correct selection of drug targets and active ingredients, the improvement of efficacy and the testing of clinical safety. These processes will be time-consuming, labor intensive and costly, making the development of new antibiotics a tremendous challenge. One approach to solve this dilemma is to screen combinations of approved drugs for those that exhibit synergistic antibacterial properties against *K. pneumoniae* infection. According to data from the U.S. Food and Drug Administration, more than 7,500 compounds have been approved for human use up to 2020. However, since 2014, only 15 new antibacterial drugs have obtained lot numbers for qualified infectious disease product (QIDP).

There thus exists a need for improved methods and compositions for treating antibiotic-resistant *Klebsiella pneumoniae* infections.

SUMMARY

Disclosed herein is a novel and unexpectedly effective therapy for the treatment of infections caused by *K. pneumoniae*, especially CRKP and Carbapenem-resistant and hypervirulent *K. pneumoniae* (CR-HvKP) that exhibited a much higher mortality rate than CRKP.

The pharmaceutical combination described herein includes a broad-spectrum antibiotic, rifampicin, and an antiviral drug, zidovudine, or pharmaceutically acceptable salts thereof. The combination method of the antibacterial drugs described herein compared with the traditional new drug development, has low cost and high efficiency, and exhibits excellent antibacterial activity both in vitro and in animal infection models.

In a first aspect, provided herein is a method of treating a *Klebsiella pneumoniae* infection in a subject in need thereof, the method comprising co-administering a therapeutically effective amount of rifampicin and zidovudine or pharmaceutically acceptable salts thereof to the subject.

In certain embodiments, the *Klebsiella pneumoniae* infection is an antibiotic-resistant *Klebsiella pneumoniae* infection.

In certain embodiments, the *Klebsiella pneumoniae* infection is a carbapenem-resistant *K. pneumoniae* (CRKP) infection.

In certain embodiments, the *Klebsiella pneumoniae* infection is a carbapenem-resistant and hypervirulent *K. pneumoniae* (CR-HvKP) infection.

In certain embodiments, rifampicin and zidovudine are each independently administered orally or by parentally.

In certain embodiments, rifampicin and zidovudine are administered in the same pharmaceutical composition.

In certain embodiments, rifampicin and zidovudine are administered in separate pharmaceutical compositions.

In certain embodiments, rifampicin and zidovudine are co-administered at a mass ratio of 1:6-6:1.

In certain embodiments, the subject is a human.

In a second aspect, provided herein is a method of disinfecting a surface, the method comprising: contacting the surface with rifampicin and zidovudine, wherein the surface is contaminated with *Klebsiella pneumoniae* or suspected of being contaminated with *Klebsiella pneumoniae*

In certain embodiments, the *Klebsiella pneumoniae* is antibiotic-resistant *K. pneumoniae*.

In certain embodiments, the *Klebsiella pneumoniae* is carbapenem-resistant *K. pneumoniae* (CRKP).

In certain embodiments, the *Klebsiella pneumoniae* is carbapenem-resistant and hypervirulent *K. pneumoniae* (CR-HvKP) infection.

In a third aspect, provided herein is a pharmaceutical composition comprising rifampicin and zidovudine or pharmaceutically acceptable salts thereof and at least one pharmaceutically acceptable excipient or pharmaceutically acceptable carrier.

In certain embodiments, the mass ratio of rifampicin to zidovudine is 1:6-6:1.

In certain embodiments, the pharmaceutical composition further comprises at least one additional antibiotic agent.

In a fourth aspect, provided herein is a kit comprising rifampicin and zidovudine or pharmaceutically acceptable salts thereof and optionally at least one additional antibiotic agent.

In certain embodiments, rifampicin and zidovudine are each present in a single pharmaceutical composition.

In certain embodiments, rifampicin and zidovudine are each present in separate pharmaceutical compositions.

In another aspect, provided herein is a pharmaceutical composition comprising rifampicin and zidovudine or pharmaceutically acceptable salts thereof.

In certain embodiments, the weight ratio of rifampicin and zidovudine or salts thereof in the pharmaceutical composition is 1:6-6:1.

In another aspect, disclosed herein is the use of the pharmaceutical composition of the first aspect described above for at least partially inhibiting the growth of *K. pneumoniae* in vitro.

In another aspect, disclosed herein is the use of the pharmaceutical composition of the first aspect in the preparation of a medicament for preventing or treating an infection caused by *K. pneumoniae* in a subject.

In certain embodiments, *K. pneumoniae* is a carbapenem-resistant *Klebsiella* sp.

In certain embodiments, *K. pneumoniae* is carbapenem-resistant and hypervirulent *K. pneumoniae*.

In certain embodiments, wherein the medicament is an injection powder or an oral dosage form.

In certain embodiments, rifampicin and zidovudine in the pharmaceutical composition at least partially inhibits the growth of *K. pneumoniae*, such as carbapenem-resistant *K. pneumoniae* in a synergistic manner.

In certain embodiments, rifampicin and zidovudine in the pharmaceutical composition at least partially inhibits the growth of carbapenem-resistant and hypervirulent *K. pneumoniae* in a synergistic manner.

In certain embodiments, wherein the subject is a human.

In another aspect, provided herein is a method comprising contacting the pharmaceutical composition of the first aspect with the surface of an object to be sterilized, wherein the bacterium is *K. pneumoniae*, preferably carbapenem-resistant *K. pneumoniae* (CRKP) or more preferably antibiotic-resistant and hypervirulent *K. pneumoniae* (CR-HvKP).

In another aspect, provided herein is a kit, wherein the kit comprises the pharmaceutical composition of the first aspect, and optionally other antibacterial agents.

BRIEF DESCRIPTION OF THE DRAWINGS

The above and other objects and features of the present disclosure will become apparent from the following description of the disclosure, when taken in conjunction with the accompanying drawings.

DETAILED DESCRIPTION

Definitions

Figure 1:
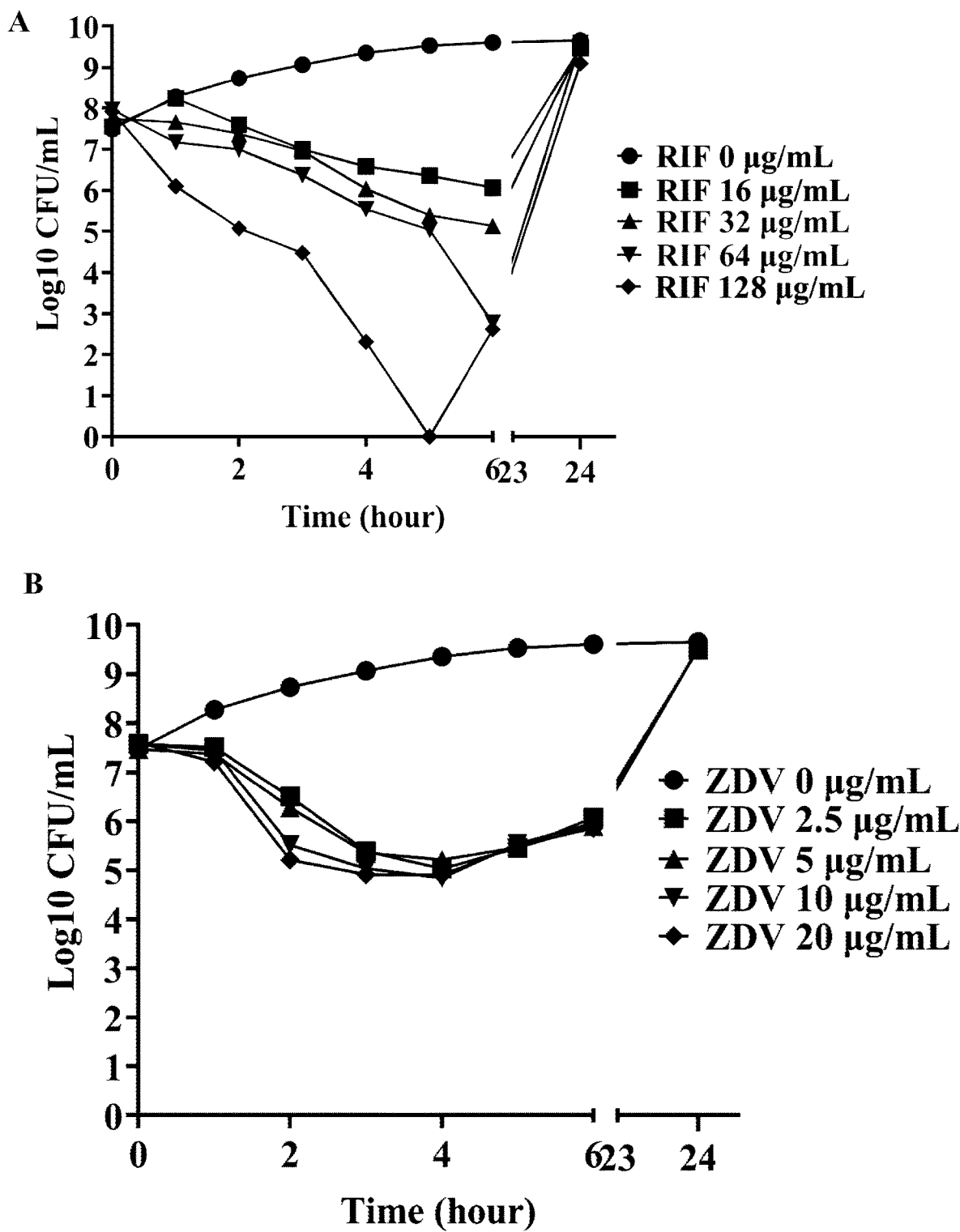
FIG. 1 depicts data demonstrating the effectiveness of zidovudine in combination with rifampicin in the treatment of CR-HvKP 1 infection and biotoxicity analysis of drug doses in vivo and in vitro. (A) CR-HvKP 1 population analysis of the time-kill curve assay with the treatment of rifampicin alone, (B) CR-HvKP 1 population analysis of the time-kill curve assay with the treatment of zidovudine alone, (C) CR-HvKP 1 population analysis of the time-kill curve assay with the treatment of rifampicin combined with zidovudine, (D) Survival curve of mice sepsis model with CR-HvkP ($\approx 3 \times 10^7$ CFU) under different drugs treatment, Log-rank (Mantel-Cox) test was performed for indicated curves (p=0.0031), (E) In vitro resistance development study against CR-HvKP 1 strain: Changes in MIC upon 6 serial passages with incremental concentrations of zidovudine, rifampicin, and a combination of both were monitored. The fold change in MIC represents the ratio of the MIC after each passage to the initial MIC before the first passage, (F) Hemolysis ratio of RBCs under treatment with different concentrations of combination drugs, (G) HepG2 cell viabilities determined by MTT assay upon treatment with different concentrations of combination drugs. The absorbance (A) value of each well was measured at $OD_{570\ nm}$, (H) AST concentration in serum of ICR mice treated by gavage with saline or 10-fold therapeutic dose of rifampicin and zidovudine combination after 7 days, (I) Histopathological section staining of kidney and liver from ICR mice treated with saline or 10-fold therapeutic dose of rifampicin and zidovudine combination after 7 days. Data represents the mean±SD (n=3); statistical analysis was operated by one-way ANOVA for multiple groups. *P<0.05, P<0.01, *P<0.001.
Figure 1:
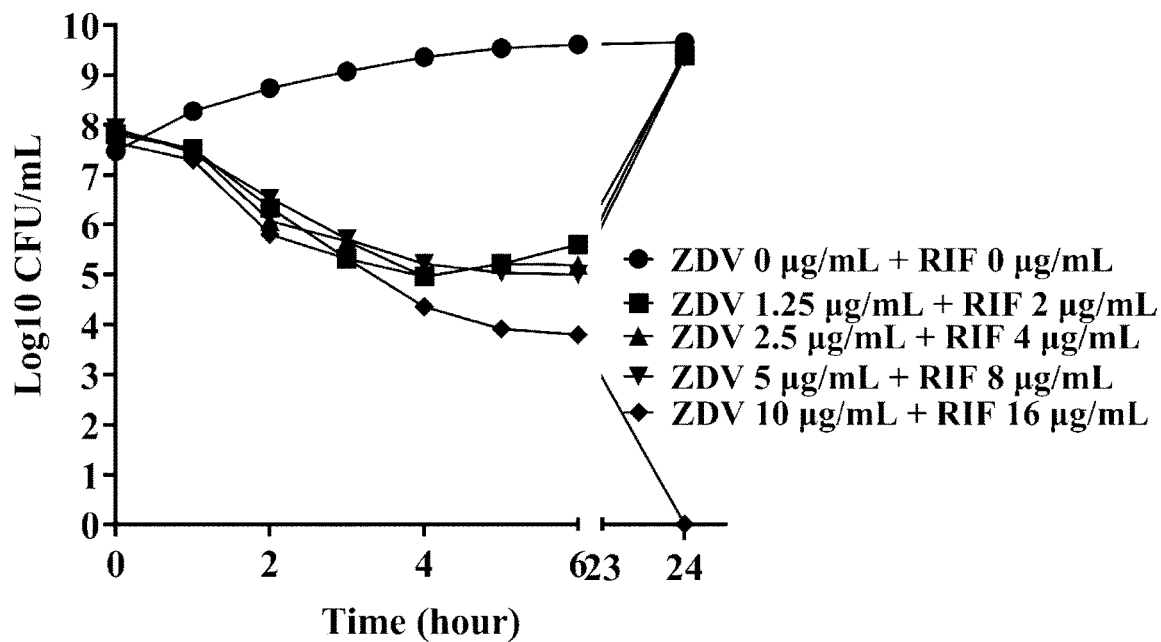
Figure 1:
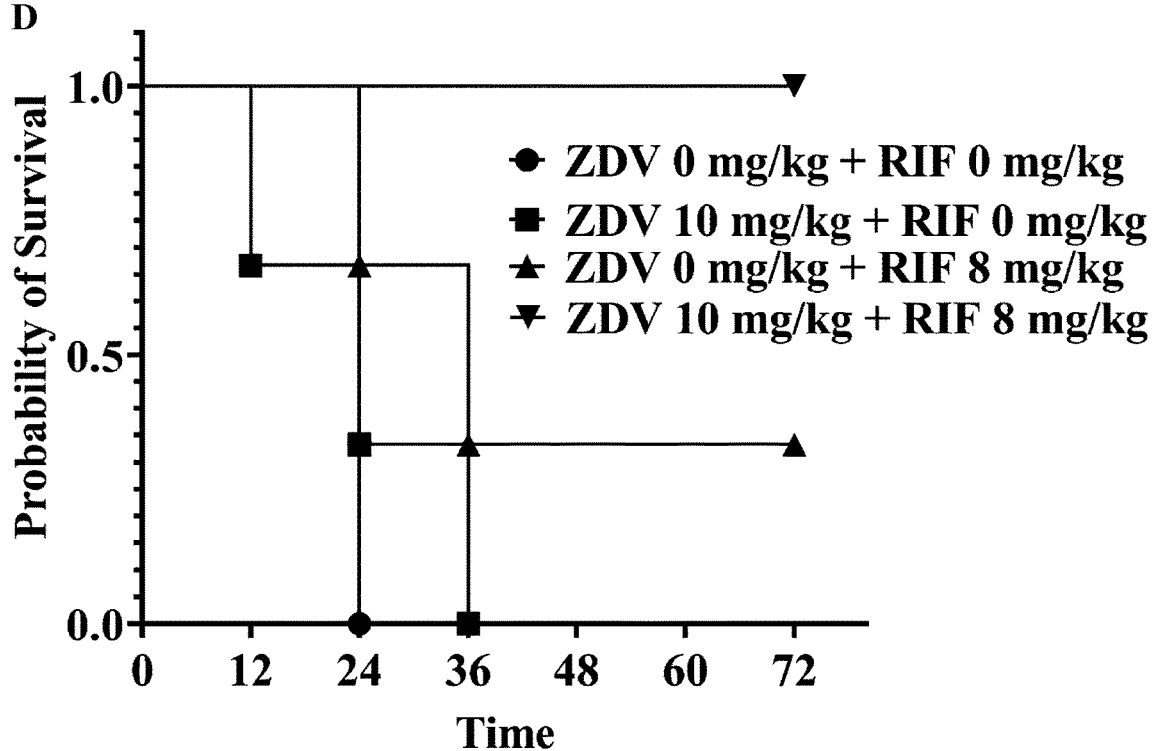
Figure 1:
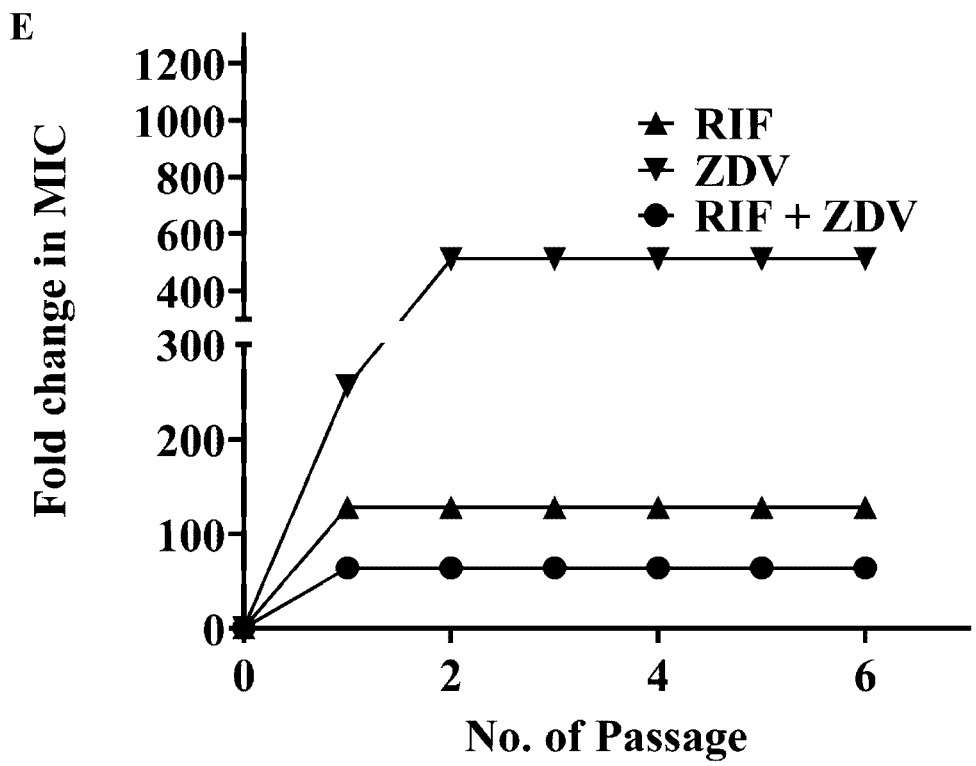
Figure 1:
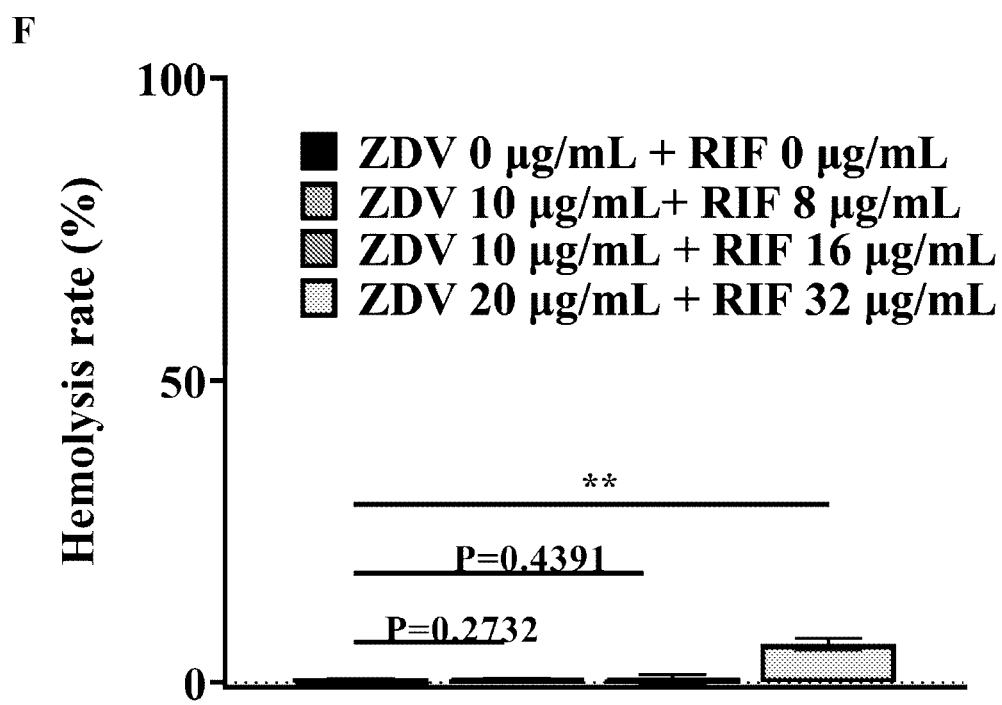
Figure 1:
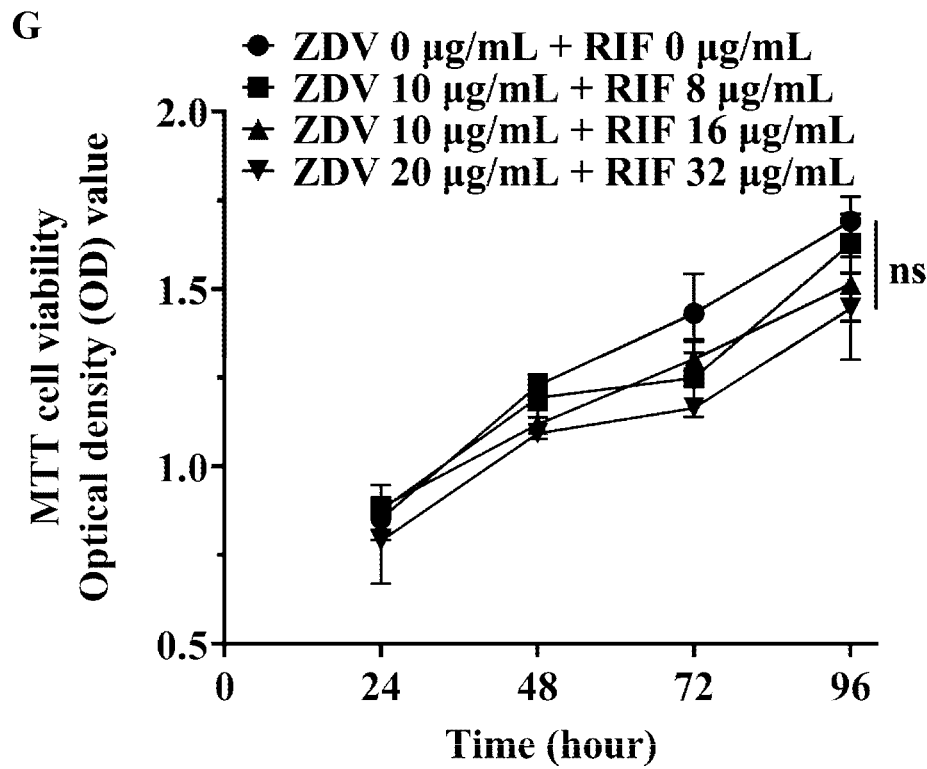
Figure 1:
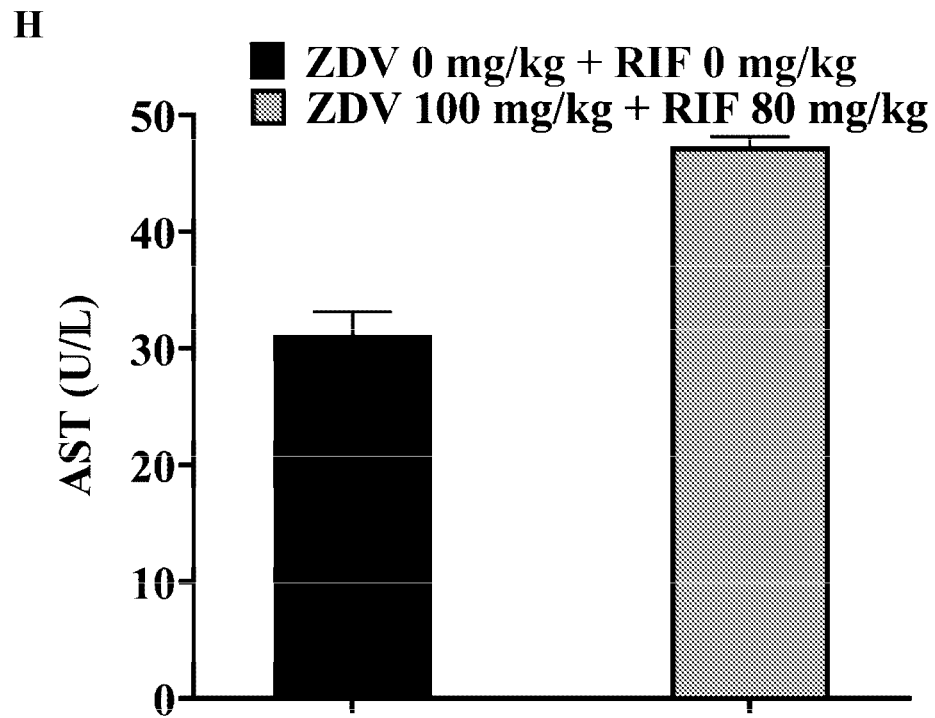
Figure 1:

The terms used in this application are well known in the art and have the following meanings:

Zidovudine is well known in the art and has the molecular structural formula:

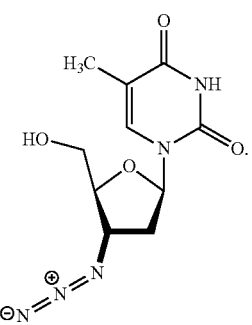 [SMILES: Cc1cn([C@H]2C[C@@H](N=[N+]=[N-])[C@@H](CO)O2)c(=O)[nH]c1=O]

Rifampicin is also well known in the art and has the molecular structural formula:

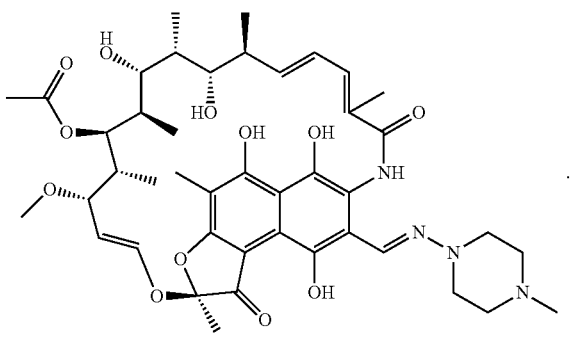 [SMILES: CO[C@H]1/C=C/O[C@@]2(C)Oc3c(C)c(O)c4c(O)c(c(/C=N/N5CCN(C)CC5)c(O)c4c3C2=O)NC(=O)/C(C)=C/C=C/[C@H](C)[C@H](O)[C@@H](C)[C@@H](O)[C@@H](C)[C@H](OC(C)=O)[C@@H]1C]

As used herein, the term "subject" refers to an animal. In certain aspects, the animal is a mammal. For example, primates, cows, sheep, goats, horses, dogs, cats, rabbits, rats, mice, and the like. In certain embodiments, the subject is a human.

As used herein, the term "inhibit", "inhibition" or "inhibiting" refers to the reduction or suppression of a given condition, symptom, or disorder, or disease, or a significant decrease in the baseline activity of a biological activity or process, or a diminishment in the viability, number or growth speed of the flora/microflora.

As used herein, the term "treat", "treating" or "treatment" of any disease or disorder refers in one embodiment, to ameliorating the disease or disorder (i.e., slowing or arresting or reducing the development of the disease or at least one of the clinical symptoms thereof). In certain embodiments, "treat", "treating" or "treatment" refers to alleviating or ameliorating at least one physical parameter including those which may not be discernible by the patient. In yet other embodiments, "treat", "treating" or "treatment" refers to modulating the disease or disorder, either physically, (e.g., stabilization of a discernible symptom), physiologically, (e.g., stabilization of a physical parameter), or both. In yet other embodiments, "treat", "treating" or "treatment" refers to preventing or delaying the onset or development or progression of the disease or disorder.

The term "therapeutically effective amount" as used herein, means that amount of the compound or pharmaceutical agent that elicits a biological and/or medicinal response in a cell culture, tissue system, subject, animal, or human that is being sought by a researcher, veterinarian, clinician, or physician, which includes alleviation of the symptoms of the disease, condition, or disorder being treated.

As used herein, the term "combinational use" includes treatment regimens in which each drug does not have to be administered by the same route of administration or at the same time. Fixed combination products are also within the scope of the invention. The administration of a pharmaceutical combination product described herein results in a beneficial effect, e.g., a synergistic therapeutic effect, compared to a monopharmacotherapy applying only one of its pharmaceutically active ingredients.

As used herein, the term "composition" encompasses separate and continuous administration of both rifampicin and zidovudine. For example, when administered continuously, zidovudine may be administered first or rifampicin may be administered first. When administered simultaneously, a composition of both is administered to the subject at the same time.

"Pharmaceutically acceptable carriers" are art-recognized and include pharmaceutically acceptable materials, compositions or vehicle, suitable for administering the compounds of the invention to mammals. The carriers include liquid or solid fillers, diluents, excipients, solvents, or encapsulating materials involved in carrying or transporting the subject agent from one organ, or portion of the body, to another organ, or portion of the body. Each carrier must be "acceptable" in the sense of being compatible with the other ingredients in the formulation and not injurious to the patient. Some examples of materials which can serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations. In some embodiments, the pharmaceutically acceptable carriers are sterilized prior to mixing with the compounds of the invention.

As used herein, the term "pharmaceutically acceptable salt" refers to those salts which are, within the scope of sound medical judgment, suitable for use in contact with the tissues of subjects without undue toxicity, irritation, allergic response and the like, and are commensurate with a reasonable benefit/risk ratio. Pharmaceutically acceptable salts are well known in the art. For example, Berge et al. describes pharmaceutically acceptable salts in detail in J. Pharmaceutical Sciences (1977) 66:1-19. Pharmaceutically acceptable salts of the compounds provided herein include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, besylate, benzoate, bisulfate, borate, butyrate, camphorate, camphorsulfonate, citrate, cyclopentanepropionate, digluconate, dodecyl sulfate, ethanesulfonate, formate, fumarate, glucoheptonate, glycerophosphate, gluconate, hemi sulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalene sulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. In certain embodiments, organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like.

Pharmaceutically acceptable salts derived from appropriate bases include alkali metal, alkaline earth metal, ammonium and $N^+(C_1$-$C_4$ alkyl$)_4$ salts. Representative alkali or alkaline earth metal salts include sodium, lithium, potassium, calcium, magnesium, iron, zinc, copper, manganese, aluminum, and the like. Further pharmaceutically acceptable salts include, when appropriate, non-toxic ammonium, quaternary ammonium, and amine cations formed using counterions, such as halide, hydroxide, carboxylate, sulfate, phosphate, nitrate, lower alkyl sulfonate, and aryl sulfonate. Organic bases from which salts can be derived include, for example, primary, secondary, and tertiary amines, substituted amines including naturally occurring substituted amines, cyclic amines, basic ion exchange resins, and the like, such as isopropylamine, trimethylamine, diethylamine, triethylamine, tripropylamine, and ethanolamine. In certain embodiments, the pharmaceutically acceptable base addition salt is chosen from ammonium, potassium, sodium, calcium, and magnesium salts.

Rifampicin and zidovudine may be formulated together in the same pharmaceutical composition optionally with any additional antibiotic agents. Alternatively, rifampicin and zidovudine may be formulated together optionally with any additional drugs in any combination in order to reduce the number of dosage forms administered to a patient. For example, rifampicin and zidovudine may be formulated in one dosage form, and an additional antibiotic agent may be formulated in another dosage form. Any of the separate dosage forms may be administered at the same or different times.

Alternatively, the compositions disclosed herein can comprise at least one additional antibiotic agent as described herein. Each component may be present in individual pharmaceutical compositions, combined pharmaceutical compositions, or in a single pharmaceutical composition.

The present disclosure is based on the unexpected discovery that co-administration of rifampicin and zidovudine exhibits substantially improved antimicrobial activity when compared to that of rifampicin or zidovudine when administered alone. Furthermore, co-administration of rifampicin and zidovudine exhibits unexpected synergistic antimicrobial activity against antibiotic-resistant *K. pneumoniae*. In addition to the unexpected biological activity, the methods and compositions described herein also exhibit low toxicity. When the methods and compositions described herein are used, the occurrence of antibiotic-resistant microorganisms can be significantly reduced.

In one aspect, provided herein is a pharmaceutical composition comprising rifampicin and zidovudine or pharmaceutically acceptable salts thereof.

In certain embodiments, the mass ratio of rifampicin and zidovudine is in the range of 1:6-6:1, e.g., in the range of 1:5-5:1, 1:4-4:1. In a specific embodiment, the mass ratio of rifampicin and zidovudine is 1:1, 1:2, 2:1, 1:4, 4:1, 4:5, 5:4, 5:8 or 8:5.

In certain embodiments, one dose of the composition comprises 0.4 g of rifampicin and 0.25 g of zidovudine, which can be prepared according to the preparation procedure of a powder injection or an oral preparation.

In certain embodiments, one dose of the composition comprises 0.4 g of rifampicin and 0.20 g of zidovudine, which can be prepared according to the preparation procedure of a lyophilized powder injection or an oral preparation.

In certain embodiments, one dose of the composition comprises 0.4 g of rifampicin and 0.5 g of zidovudine, which can be prepared according to the preparation procedure of a powder injection or an oral preparation.

In certain embodiments, one dose of the composition comprises 0.2 g of rifampicin and 0.4 g of zidovudine, which can be prepared according to the preparation procedure of a lyophilized powder injection or an oral preparation.

In certain embodiments, one dose of the composition comprises 0.8 g of rifampicin and 0.5 g of zidovudine, which can be prepared according to the preparation procedure of a powder injection or an oral preparation.

In certain embodiments, one dose of the composition comprises 0.5 g of rifampicin and 0.8 g of zidovudine, which can be prepared according to the preparation procedure of a lyophilized powder injection or an oral preparation.

In certain embodiments, one dose of the composition comprises 0.8 g of rifampicin and 1 g of zidovudine, which can be prepared according to the preparation procedure of a powder injection or an oral preparation.

In certain embodiments, one dose of the composition comprises 0.3 g of rifampicin and 0.6 g of zidovudine, which can be prepared according to the preparation procedure of a lyophilized powder injection or an oral preparation.

In certain embodiments, one dose of the composition comprises 1.6 g of rifampicin and 0.8 g of zidovudine, which can be prepared according to the preparation procedure of a powder injection or an oral preparation.

In certain embodiments, one dose of the composition comprises 1.6 g of rifampicin and 1 g of zidovudine, which can be prepared according to the preparation procedure of a lyophilized powder injection or an oral preparation.

In certain embodiments, one dose of the composition comprises 1.6 g of rifampicin and 2 g of zidovudine, which can be prepared according to the preparation procedure of a powder injection or an oral preparation.

In certain embodiments, one dose of the composition comprises 2 g of rifampicin and 1.6 g of zidovudine, which can be prepared according to the preparation procedure of a lyophilized powder injection or an oral preparation.

In another aspect, disclosed herein is the use of the composition of the first aspect described above for killing or at least partially inhibiting the growth of *K. pneumoniae*, such as carbapenem-resistant *K. pneumoniae* (CRKP), or carbapenem-resistant and hypervirulent *K. pneumoniae* (CR-HvKP) in vitro.

In another aspect, disclosed herein is the use of the composition of the first aspect in the preparation of a pharmaceutical composition for preventing or treating an infection caused by *K. pneumoniae* in a subject.

The present disclosure also provides a method of treating a *Klebsiella pneumoniae* infection in a subject in need thereof, the method comprising co-administering a therapeutically effective amount of rifampicin and zidovudine or pharmaceutically acceptable salts thereof to the subject.

Rifampicin and zidovudine may be administered concurrently (e.g., simultaneously, essentially simultaneously or within the same treatment protocol) or sequentially, depending upon the nature of the bacterial infection and the condition of the patient.

If rifampicin and zidovudine are not administered simultaneously or essentially simultaneously, then the optimum order of administration of rifampicin described herein and zidovudine, may be different for different bacterial infections. Thus, in certain situations rifampicin described may be administered first followed by zidovudine; and in other situations, zidovudine may be administered first followed by the administration of rifampicin. This alternate administration may be repeated during a single treatment protocol. The determination of the order of administration, and the number of repetitions of administration of each therapeutic agent during a treatment protocol, is well within the knowledge of the skilled physician after evaluation of the disease being treated and the condition of the patient.

The *Klebsiella pneumoniae* may be antibiotic-resistant *Klebsiella pneumoniae*. In certain embodiments, the *Klebsiella pneumoniae* is CRKP or CR-HvKP. In certain embodiments, the *Klebsiella pneumoniae* carries one or more carbapenemase genes selected from the group consisting of $bla_{NDM-1}$, $bla_{KPC}$ and $bla_{OXA-48}$.

In certain embodiments, the method further comprises co-administering one or more additional antibiotics to the subject. Exemplary antibiotics useful in the present methods include, but are not limited to, (1) macrolides or ketolides such as erythromycin, azithromycin, clarithromycin and telithromycin; (2) beta-lactams including penicillins such as penicillin G, penicillin V, methicillin, oxacillin, cloxacillin, dicloxacillin, nafcillin, ampicillin, amoxicillin, carbenicillin, ticarcillin, mezlocillin, piperacillin, azlocillin, temocillin, cephalosporins such as cepalothin, cephapirin, cephradine, cephaloridine, cefazolin, cefamandole, cefuroxime, cephalexin, ceçrozil, cefaclor, loracarbef, cefoxitin, cefinetazole, cefotaxime, ceftizoxime, ceftriaxone, cefoperazone, ceftazidime, cefixime, cefpodoxime, ceftibuten, cefdinir, cerpirome, cefepime, and carbapenems such as doripenem, imipenem, meropenem and PZ-601; (3) glycopeptides such as vancomycin and teicoplanin; (4) quinolones such as nalidixic acid, oxolinic acid, norfloxacin, pefloxacin, enoxacin, ofloxacin, levofloxacin, ciprofloxacin, temafloxacin, lomefloxacin, fleroxacin, grepafloxacin, sparfloxacin, trovafloxacin, clinafloxacin, gatifloxacin, moxifloxacin, sitafloxacin, ganefloxacin, gemifloxacin and pazufloxacin; (5) antibacterial suffonanmides and antibacterial sulphanilamides, including para-aminobenzoic acid, sulfadiazine, sulfisoxazole, sulfamethoxazole and sulfathalidine; (6) aminoglycosides such as streptomycin, neomycin, kanamycin, paromycin, gentamicin, tobramycin, amikacin, netilmicin, spectinomycin, dibekalin and isepamicin; (7) tetracyclines such as tetracycline, chlortetracycline, demeclocycline, minocycline, oxytetracycline, methacycline, doxycycline, tigecycline; (8) rifamycins such as rifapentine, rifabutin, bezoxazinorifamycin and rifaximin; (9) lincosamides such as lincomycin and clindamycin; (10) streptogramins such as quinupristin and daflopristin; (11) oxazolidinones such as linezolid or tedizolid; (12) polymyxin, colistin and polymyxin E; (13) trimethoprim and bacitracin; (14) efflux pump inhibitors; and (15) beta-lactamase inhibitors, including avibactam and its analogs.

In certain embodiments, the above-described pharmaceutical composition is used to inhibit antibiotic-resistant *K. pneumoniae*, such as carbapenem-resistant *Klebsiella* sp. (CRKP) or carbapenem-resistant and hypervirulent *K. pneumoniae* (CR-HvKP) in vitro.

In humans, *Klebsiella* interactions range from opportunistic pathogens (mainly in hospitalized patients and community-acquired infections) to asymptomatic carriers that occur frequently in the intestinal tract and less frequently in the nasopharynx. As a nosocomial infection, *Klebsiella* is primarily associated with urinary tract and respiratory infections, as well as wound and soft tissue infections that may cause fatal septicemia. The scope of clinical syndromes includes bacteremia, pneumonia, urinary tract infection (UTI), thrombophlebitis, upper respiratory tract infection, cholecystitis, wound infection, osteomyelitis, endogenous endophthalmitis, endophthalmitis, endocarditis and meningitis.

In a fourth aspect, provided herein is a method comprising contacting the pharmaceutical composition of the first aspect with a surface to be sterilized. In certain embodiments, *K. pneumoniae*, such as Carbapenem-resistant *K. pneumoniae* (CRKP) or antibiotic-resistant and hypervirulent *K. pneumoniae* (CR-HvKP) is on the surface to be sterilized or suspected of being on the surface to be sterilized.

In a fifth aspect, the present disclosure provides a kit comprising rifampicin and zidovudine for use in inhibiting the growth of or killing *K. pneumoniae*.

In certain embodiments, the kit optionally includes one or more additional antibacterial agents.

Also provided herein are pharmaceutical compositions comprising rifampicin and zidovudine or pharmaceutically acceptable salts thereof, and a pharmaceutically acceptable adjuvant, diluent or carrier. Such pharmaceutical composition being useful for treating microbial infections, particularly for inhibiting the growth of or killing *K. pneumoniae*.

As used herein, "killing" means a loss of viability as assessed by a lack of metabolic activity.

As used herein, the term "microorganism" means a bacterium. "Microbial infection" means any bacterial infection. Preferably, the term "microbial" in these contexts, means "bacterial". In certain embodiments, the bacterial infection treated by the compositions described herein is a Gram-negative infection.

In certain embodiments, the bacteria is *Klebsiella* spp. (e.g. *K. pneumoniae* and *K. oxytoca*). The methods and compositions described herein are particularly advantageous for the treatment of antibiotic-resistant *Klebsiella* spp. The microbial infection for which the pharmaceutical compositions comprising rifampin and zidovudine provided herein can be used for treatment of an infection caused by one or more of *E. coli, K. pneumoniae* or one of the KES (*Klebsiella, Enterobacter* and *Serratia*) group bacteria. The pharmaceutical compositions provided herein can be used to treat infections caused by CRKP or CR-HvKP. In certain embodiments, rifampicin and zidovudine act synergistically against antibiotic-resistant *K. pneumoniae*.

Rifampicin and zidovudine may be administered in pure form or as one or more pharmaceutical compositions to a subject in need thereof.

Pharmaceutical compositions include those suitable for oral, parenteral (including subcutaneous e.g. by injection or by depot tablet, intradermal, intrathecal, intramuscular e.g. by depot and intravenous), rectal and topical (including dermal, buccal and sublingual) or in a form suitable for administration by inhalation or insufflation administration. The most suitable route of administration may depend on the condition and disorder of the patient.

The pharmaceutical compositions may conveniently be presented in unit dosage form and may be prepared by any of the methods well known in the art of pharmacy, e.g., as described in "Remington: The Science and Practice of Pharmacy", Lippincott Williams & Wilkins, 21st Edition, (2005). Suitable methods include the step of bringing into association the active ingredients with the carriers which constitute one or more excipients. In general, the pharmaceutical compositions are prepared by uniformly and intimately bringing into association the active ingredients with liquid carriers or finely divided solid carriers or both, and then, if necessary, shaping the product into the desired dosage form. It will be appreciated that when rifampicin and zidovudine are administered independently, each may be administered by a different means.

When formulated with excipients, the active ingredients may be present in a concentration from 0.1 to 99.5% (such as from 0.5 to 95%) by weight of the total mixture; conveniently from 30 to 95% for tablets and capsules and 0.01 to 50% (such as from 3 to 50%) for liquid preparations.

Pharmaceutical compositions suitable for oral administration may be presented as discrete units such as capsules, cachets or tablets (e.g. chewable tablets in particular for pediatric administration), each containing a predetermined amount of active ingredient; as powder or granules; as a solution or suspension in an aqueous liquid or non-aqueous liquid; or as an oil-in-water liquid emulsion or water-in-oil liquid emulsion. The active ingredients may also be presented as a bolus, electuary or paste.

A tablet may be made by compression or molding, optionally with one or more excipients. Compressed tablets may be prepared by compressing in a suitable machine the active ingredients in a free-flowing form such as a powder or granules, optionally mixed with other conventional excipients such as binding agents (e.g. syrup, acacia, gelatin, sorbitol, tragacanth, mucilage of starch, polyvinylpyrrolidone and/or hydroxymethyl cellulose), fillers (e.g. lactose, sugar, microcrystalline cellulose, maize-starch, calcium phosphate and/or sorbitol), lubricants (e.g. magnesium stearate, stearic acid, talc, polyethylene glycol and/or silica), disintegrants (e.g. potato starch, croscarmellose sodium and/or sodium starch glycolate) and wetting agents (e.g. sodium lauryl sulphate). Molded tablets may be made by molding in a suitable machine a mixture of the powdered active ingredients with an inert liquid diluent. The tablets may be optionally coated or scored and may be formulated so as to provide controlled release (e.g. delayed, sustained, or pulsed release, or a combination of immediate release and controlled release) of the active ingredients.

Alternatively, the active ingredients may be incorporated into oral liquid preparations such as aqueous or oily suspensions, solutions, emulsions, syrups or elixirs. Pharmaceutical compositions containing the active ingredients may also be presented as a dry product for constitution with water or another suitable carrier before use. Such liquid preparations may contain conventional additives such as suspending agents (e.g. sorbitol syrup, methyl cellulose, glucose/sugar syrup, gelatin, hydroxymethyl cellulose, carboxymethyl cellulose, aluminum stearate gel and/or hydrogenated edible oils), emulsifying agents (e.g. lecithin, sorbitan mono-oleate and/or acacia), non-aqueous carriers (e.g. edible oils, such as almond oil, fractionated coconut oil, oily esters, propylene glycol and/or ethyl alcohol), and preservatives (e.g. methyl or propyl p-hydroxybenzoates and/or sorbic acid).

Methods of producing topical pharmaceutical compositions, such as creams, ointments, lotions, sprays and sterile aqueous solutions or suspensions are well known in the art. Suitable methods of preparing topical pharmaceutical compositions are described, e.g. in WO9510999, U.S. Pat. No. 6,974,585, WO2006048747, as well as in documents cited in any of these references.

Pharmaceutical compositions for use according to the methods described herein may be presented in a pack or dispenser device which may contain one or more unit dosage forms comprising the active ingredients. The pack may, for example, comprise metal or plastic foil, such as a blister pack. Where the compositions are intended for administration as two separate compositions, these may be presented in the form of a twin pack.

Pharmaceutical compositions may also be prescribed to the patient in "patient packs" containing the whole course of treatment in a single package, usually a blister pack. Patient packs have an advantage over traditional prescriptions, where a pharmacist divides a patients' supply of a pharmaceutical from a bulk supply, in that the patient always has access to the package insert contained in the patient pack, normally missing in traditional prescriptions. The inclusion of the package insert has been shown to improve patient compliance with the physician's instructions.

The administration of rifampicin and zidovudine by means of a single patient pack, or patient packs of each composition, including a package insert directing the patient to the correct use of the invention is a desirable feature of this invention.

The pharmaceutical composition or kit described herein may also comprises one or more additional antibiotics. Exemplary antibiotics useful in the present pharmaceutical compositions include, but are not limited to, (1) macrolides or ketolides such as erythromycin, azithromycin, clarithromycin and telithromycin; (2) beta-lactams including penicillins such as penicillin G, penicillin V, methicillin, oxacillin, cloxacillin, dicloxacillin, nafcillin, ampicillin, amoxicillin, carbenicillin, ticarcillin, mezlocillin, piperacillin, azlocillin, temocillin, cephalosporins such as cepalothin, cephapirin, cephradine, cephaloridine, cefazolin, cefamandole, cefuroxime, cephalexin, cefprozil, cefaclor, loracarbef, cefoxitin, cefmetazole, cefotaxime, ceftizoxime, ceftriaxone, cefoperazone, ceftazidime, cefixime, cefpodoxime, ceftibuten, cefdinir, cerpirome, cefepime, and carbapenems such as doripenem, imipenem, meropenem and PZ-601; (3) glycopeptides such as vancomycin and teicoplanin; (4) quinolones such as nalidixic acid, oxolinic acid, norfloxacin, pefloxacin, enoxacin, ofloxacin, levofloxacin, ciprofloxacin, temafloxacin, lomefloxacin, fleroxacin, grepafloxacin, sparfloxacin, trovafloxacin, clinafloxacin, gatifloxacin, moxifloxacin, sitafloxacin, ganefloxacin, gemifloxacin and pazufloxacin; (5) antibacterial suffonanmides and antibacterial sulphanilamides, including para-aminobenzoic acid, sulfadiazine, sulfisoxazole, sulfamethoxazole and sulfathalidine; (6) aminoglycosides such as streptomycin, neomycin, kanamycin, paromycin, gentamicin, tobramycin, amikacin, netilmicin, spectinomycin, dibekalin and isepamicin; (7) tetracyclines such as tetracycline, chlortetracycline, demeclocycline, minocycline, oxytetracycline, methacycline, doxycycline, tigecycline; (8) rifamycins such as rifapentine, rifabutin, bezoxazinorifamycin and rifaximin; (9) lincosamides such as lincomycin and clindamycin; (10) streptogramins such as quinupristin and daflopristin; (11) oxazolidinones such as linezolid or tedizolid; (12) polymyxin, colistin and polymyxin E; (13) trimethoprim and bacitracin; (14) efflux pump inhibitors; and (15) beta-lactamase inhibitors, including avibactam and its analogs.

The aforementioned antibiotic agents may be administered in combination with rifampicin and zidovudine, wherein these antibiotic agents are administered prior to, simultaneously, or after rifampicin and zidovudine. When simultaneous administration of rifampicin and zidovudine with an additional antibiotic agent is desired and the route of administration is the same, then rifampicin and zidovudine may be formulated in the same dosage form together with the additional antibiotic agent. An example of a dosage form containing rifampicin and zidovudine and an additional antibiotic agent is intravenous administration. Another example is the oral administration of a solution comprising rifampicin and zidovudine and at least one additional antibiotic agent.

In certain embodiments, the pharmaceutical compositions described herein comprises at least one pharmaceutically acceptable carrier or excipient.

EXAMPLES

The pharmaceutical compounds used in screening of the were from a commercial drug library (Selleckchem, Drug library L1300). The carbapenem-resistant K. pneumoniae (CRKP) and carbapenem-resistant and hypervirulent K. pneumoniae (CR-HvKP) strains used were isolated, identified, and published in Gu et al., A fatal outbreak of ST11 carbapenem-resistant hypervirulent Klebsiella pneumoniae in a Chinese hospital: a molecular epidemiological study. The Lancet infectious diseases, 2018, 18(1): 37-46, and Yang et al., Molecular epidemiology of carbapenem-resistant hypervirulent Klebsiella pneumoniae in China, Emerging microbes & infections, 2022, 11(1): 841-849. See Table 1 below for information on the strains. The model bacterium E. coli ATCC25922 and K. pneumoniae MGH78578, other cells and experimental materials are all commercially available.

TABLE 1

Strains Tested

| Bacteria | NCBI registration numbers | CR-HvKP/CRKP |
|---|---|---|
| CR-HvKP 1 | PRJNA391211 | CR-HvKP |
| CR-HvKP 2 | PRJNA391211 | CR-HvKP |
| CR-HvKP 3 | PRJNA391211 | CR-HvKP |
| CR-HvKP 5 | PRJNA391211 | CR-HvKP |
| 14WZ-43 | PRJNA503173 | CR-HvKP |
| 14WZ-44 | PRJNA503173 | CRKP |
| 14WZ-45 | PRJNA503173 | CR-HvKP |
| 14WZ-51 | PRJNA503173 | CR-HvKP |
| 14WZ-52 | PRJNA503173 | CR-HvKP |
| 15WZ-68 | PRJNA503173 | CR-HvKP |
| 15WZ-88 | PRJNA503173 | CR-HvKP |
| 16WZ-134 | PRJNA503173 | CR-HvKP |
| 16ZR-10 | PRJNA503173 | CR-HvKP |
| 16ZR-33 | PRJNA503173 | CR-HvKP |
| 16ZR-58 | PRJNA503173 | CR-HvKP |
| 16ZR-93 | PRJNA503173 | CR-HvKP |
| 17ZR-31 | PRJNA503173 | CR-HvKP |
| 17ZR-61 | PRJNA503173 | CR-HvKP |
| 17ZR-63 | PRJNA503173 | CR-HvKP |
| 17ZR-75 | PRJNA503173 | CR-HvKP |
| MGH78578 | commercial strain | K. pneumoniae |
| ATCC25922 | commercial strain | E. coli |

Screening for Zidovudine

Over 1,500 FDA-approved pharmaceutical compounds from a commercial drug library (Selleckchem, Drug library L1300) (Xue et al., Tumour cells are sensitized to ferroptosis via RB 1CC1-mediated transcriptional reprogramming. Clinical and Translational Medicine, 2022, 12(2): e747, https://doi.org/10.1002/ctm2.747) were screened. Zidovudine exhibited antibacterial effect on various species of Gram-negative bacteria including, E. coli, P. aeruginosa, Salmonella spp., and K. pneumoniae.

Subsequently, the minimum inhibitory concentrations (MICs) of rifampicin and zidovudine were determined by testing against the strains in Table 1 above. The method is briefly described as follows: The MIC of zidovudine on bacteria was determined according to CLSI guidelines. Bacterial strains grown on MH agar plates were resuspended in sterilized 0.85% sodium chloride solution. The turbidity of the bacterial cell suspension was adjusted according to McFarland Standard No. 0.5 and inoculated into MH broth (Sigma Chemical Company, USA) containing zidovudine in various concentration gradients. All tested culture media were finally cultured at 37° C. for 16 hours. E. coli ATCC25922 and K. pneumoniae MGH78578 in Table 1 were used as reference control bacteria. See Table 2 below for MIC results.

Determination of Synergy

This experiment detected the synergistic antibacterial effect of rifampicin and zidovudine. The method is as described above, with the difference being in the addition of combinations of zidovudine and/or rifampicin at different concentrations. As a result, it was found that when rifampicin was used in combination with zidovudine, all strains except E. coli in Table 1 exhibited significantly lower MICs than rifampicin and zidovudine alone, i.e. exhibited synergistic antibacterial effect. See Table 2 and Table 2-1 below for details.

TABLE 2

Minimum inhibitory concentrations (MICs) of rifampicin (RIF) alone, zidovudine (ZDV) alone, and combinations of RIF and ZDV on clinical carbapenem-resistant hypervirulent K. pneumoniae.

| | Minimum inhibitory concentration MIC (µg/mL) | | | | | |
|---|---|---|---|---|---|---|
| | | | RIF and ZDV (mass ratio = 1:1) | | RIF and ZDV (mass ratio = 1:4) | |
| Bacteria | RIF | ZDV | RIF | ZDV | RIF | ZDV |
| CR-HvKP 1 | 32 | 2.5 | 0.5 | 0.5 | 0.0625 | 0.25 |
| CR-HvKP 2 | 32 | 2.5 | 0.5 | 0.5 | 0.125 | 0.5 |
| CR-HvKP 3 | 32 | 2.5 | 0.5 | 0.5 | 0.125 | 0.5 |
| CR-HvKP 5 | 32 | 5 | 0.25 | 0.25 | 0.125 | 0.5 |
| 14WZ-43 | 32 | 2.5 | 0.5 | 0.5 | 0.25 | 1 |
| 14WZ-44 | 32 | 2.5 | 0.5 | 0.5 | 0.0625 | 0.25 |
| 14WZ-45 | 16 | 2.5 | 0.5 | 0.5 | 0.125 | 0.5 |
| 14WZ-51 | 32 | 2.5 | 1 | 1 | 0.125 | 0.5 |
| 14WZ-52 | 32 | 1.25 | 0.5 | 0.5 | 0.125 | 0.5 |
| 15WZ-68 | 32 | 2.5 | 2 | 2 | 0.25 | 1 |
| 15WZ-88 | 16 | 2.5 | 0.5 | 0.5 | 0.25 | 1 |
| 16WZ-134 | 32 | >20 | 0.5 | 0.5 | 0.125 | 0.5 |
| 16ZR-10 | 32 | 0.625 | 0.125 | 0.125 | 0.03125 | 0.125 |
| 16ZR-33 | 16 | 5 | 1 | 1 | 0.25 | 1 |
| 16ZR-58 | 32 | 2.5 | 0.5 | 0.5 | 0.125 | 0.5 |
| 16ZR-93 | >64 | >20 | 4 | 4 | 4 | 16 |
| 17ZR-31 | 32 | 2.5 | 1 | 1 | 0.25 | 1 |
| 17ZR-61 | 32 | 1.25 | 0.5 | 0.5 | 0.125 | 0.5 |
| 17ZR-63 | 32 | 1.25 | 1 | 1 | 0.25 | 1 |
| 17ZR-75 | 64 | 5 | 2 | 2 | 0.5 | 2 |
| MGH78578 | 32 | 5 | 2 | 2 | 0.5 | 2 |
| ATCC25922 | 8 | 0.625 | 1 | 1 | 0.25 | 1 |

TABLE 2-1

Minimum inhibitory concentrations (MICs) of rifampicin (RIF) alone, zidovudine (ZDV) alone, and combinations of RIF and ZDV on clinical carbapenem-resistant hypervirulent *K. pneumoniae*.

| | Minimum inhibitory concentration MIC (µg/mL) | | | | | | | |
|---|---|---|---|---|---|---|---|---|
| | | | RIF and ZDV (mass ratio = 4:1) | | RIF and ZDV (mass ratio = 5:8) | | RIF and ZDV (mass ratio = 8:5) | |
| Bacteria | RIF | ZDV | RIF | ZDV | RIF | ZDV | RIF | ZDV |
| CR-HvKP 1 | 32 | 2.5 | 2 | 0.5 | 0.15625 | 0.25 | 0.5 | 0.3125 |
| CR-HvKP 2 | 32 | 2.5 | 2 | 0.5 | 0.625 | 1 | 0.25 | 0.15625 |
| CR-HvKP 3 | 32 | 2.5 | 2 | 0.5 | 0.3125 | 0.5 | 1 | 0.625 |
| CR-HvKP 5 | 32 | 5 | 1 | 0.25 | 0.3125 | 0.5 | 0.5 | 0.3125 |
| 14WZ-43 | 32 | 2.5 | 4 | 1 | 0.625 | 1 | 0.5 | 0.3125 |
| 14WZ-44 | 32 | 2.5 | 1 | 0.25 | 0.078125 | 0.125 | 1 | 0.625 |
| 14WZ-45 | 16 | 2.5 | 1 | 0.25 | 0.078125 | 0.125 | 0.5 | 0.3125 |
| 14WZ-51 | 32 | 2.5 | 4 | 1 | 0.3125 | 0.5 | 0.5 | 0.3125 |
| 14WZ-52 | 32 | 1.25 | 2 | 0.5 | 0.625 | 1 | 0.5 | 0.3125 |
| 15WZ-68 | 32 | 2.5 | 2 | 0.5 | 1.25 | 2 | 1 | 0.625 |
| 15WZ-88 | 16 | 2.5 | 2 | 0.5 | 0.625 | 1 | 0.5 | 0.3125 |
| 16WZ-134 | 32 | >20 | 4 | 1 | 0.3125 | 0.5 | 1 | 0.625 |
| 16ZR-10 | 32 | 0.625 | 0.5 | 0.125 | 0.15625 | 0.25 | 0.5 | 0.3125 |
| 16ZR-33 | 16 | 5 | 1 | 0.25 | 0.625 | 1 | 2 | 1.25 |
| 16ZR-58 | 32 | 2.5 | 2 | 0.5 | 0.3125 | 0.5 | 1 | 0.625 |
| 16ZR-93 | >64 | >20 | 4 | 1 | 2.5 | 4 | 4 | 2.5 |
| 17ZR-31 | 32 | 2.5 | 2 | 0.5 | 0.3125 | 0.5 | 2 | 1.25 |
| 17ZR-61 | 32 | 1.25 | 2 | 0.5 | 0.3125 | 0.5 | 1 | 0.625 |
| 17ZR-63 | 32 | 1.25 | 2 | 0.5 | 0.625 | 1 | 1 | 0.625 |
| 17ZR-75 | 64 | 5 | 4 | 1 | 0.625 | 1 | 2 | 1.25 |
| MGH78578 | 32 | 5 | 4 | 1 | 0.625 | 1 | 2 | 1.25 |
| ATCC25922 | 8 | 0.625 | 2 | 0.5 | 0.625 | 1 | 2 | 1.25 |

Time-Kill Curve Assay

The susceptibility of the test strains to rifampicin and zidovudine was determined using time-kill experiments. CR-HvKP 1 was selected as the representative strain. The method is briefly described as follows: A single colony was inoculated into 5 mL of MH broth and cultured overnight at 37° C. The overnight culture was subcultured into 5 mL of fresh MH broth with a 1% inoculum volume and cultured with shaking at 37° C. until an optical density of 0.3 (about $1 \times 10^8$ CFU/mL) was reached. Then, a series of concentration gradients of rifampicin, zidovudine, and combinations of zidovudine and rifampicin were added in the culture media respectively, and allowed to continue culturing. A small portion of the test culture was taken at various time intervals, dropped on MH agar plates, and incubated overnight at 37° C. The number of colonies was recorded by CFU counting method. Time-kill curves were generated by plotting the Log 10 of CFU/mL versus time using Graphpad Prism 8.0 (San Diego, CA) software. All drug sensitive tests were performed in triplicate to ensure consistency.

Time-kill curve assay showed that at 20 µg/mL zidovudine, the population size of CR-HvKP 1 was reduced in the first 4 hours and then re-grew to reach the same size as no treatment control at 24 hours; at 128 µg/mL of rifampicin, the bacterial population reduced at 6 hours, but regrew after 24 hours, suggesting that CR-HvKP 1 may develop resistance to zidovudine or rifampicin after long term treatment (FIGS. 1A, 1B). When zidovudine and rifampicin were simultaneously present at 10 µg/mL and 16 µg/mL respectively, CR-HvKP 1 could be eradicated within 24 hours, confirming the synergistic antimicrobial effect of these two drugs was strong (FIG. 1C).

Mouse Experiment

The synergistic antimicrobial effect of rifampicin and zidovudine was further tested in the murine infection model. The ICR mice were injected with $3 \times 10^7$ CFU of CR-HvKP 1 intraperitoneally to create sepsis infection models. Treatment of different combinations of rifampicin and zidovudine were applied to the mice through oral gavage at 1-hour post-infection and every 12-hour intervals. The mortality rate of mice without any treatment was 100% in 24 hours. For the experimental group treated with zidovudine (10 mg/kg) only, the mortality rate of mice was 100% in 36 hours. For the experimental group treated with rifampicin (8 mg/kg) only, the mortality rate of mice was 66% in 72 hours. Importantly, all mice in the experimental group treated with a combination of zidovudine (10 m/kg) and rifampicin (8 mg/kg) survived for 72 hours. See Table 2. This result showed that the efficacy of simultaneous usage of rifampicin and zidovudine was much higher than that of each of the two agents when used alone in the murine model (FIG. 1D).

TABLE 3

The therapeutic effect of zidovudine combined with rifampicin on carbapenem-resistant and hypervirulent *K. pneumoniae* CR-HvKP 1 infected ICR mice.

| Treatment Method | Viability (%) |
|---|---|
| ZDV 0 mg/kg + RIF 0 mg/kg | 0 |
| ZDV 0 mg/kg + RIF 8 mg/kg | 30 |
| ZDV 10 mg/kg + RIF 0 mg/kg | 0 |
| ZDV 10 mg/kg + RIF 8 mg/kg | 100 |

Resistance Development Test

A resistance development test was performed to assess the rate of drug-induced resistance in *K. pneumoniae* by rifampicin, zidovudine, or a combination of both. The principle of this experiment is that sub-inhibitory concentrations of antibiotics will induce drug-resistant mutations of bacteria.

Materials and methods: CR-HvKP 1 was selected as the representative strain. Bacterial cells (OD=0.1) were first grown in 5 mL of LB broth containing sub-inhibitory concentrations (1/2 MIC) of rifampicin, zidovudine or rifampicin+zidovudine combination. After 24 hours of culture, the culture possibly containing drug-resistant mutant bacteria was diluted 1:100 into fresh LB medium containing 2-fold concentration of drugs. This continuous transfer was repeated for six generations, i.e. the experiment was conducted for six days (the concentration on the second day was twice that on the first day, with daily increment). The MIC of rifampicin and zidovudine, or both in combination, was determined for each generation of culture using the MIC method according to CLSI guidelines.

The results showed that incubation of rifampicin or zidovudine with CR-HvKP 1 led to an increase in MIC to 4096 μg/mL and 1280 μg/mL by the first or second generation, respectively, while combinational use of these two drugs led to an increase in MIC to 32 μg/mL+20 μg/mL in 6 days, a much slower resistance development rate when compared to single use of drugs (FIG. 1E).

Toxicity Test

In-vitro method: Hemolysis experiment: The blood from fresh ICR mice was collected by cardiac blood withdrawal, preserved in K2-EDTA tubes (BD Vacultainer® K2 EDTA, Becton-Dickinson) and temporarily stored at 4° C. The whole blood sample was centrifuged (500 g, 10 minutes) to remove plasma, and then washed three times with PBS buffer. After the last washing, 100 μL of the remaining red blood cells (RBCs) were carefully aspirated from the bottom and diluted with 4.9 mL PBS buffer to prepare a 2% blood solution. 50 μL of diluted RBCs were then mixed with the drug (rifampicin alone (32, 16, 8 μg/mL) or rifampicin in combination with zidovudine in PBS (100 μL)). 50 μL of diluted RBCs were mixed with 100 μL of milli-Q $H_2O$ (100% hemolysis) or 100 μL of drug-free PBS as positive and negative controls, respectively. It should be noted that rifampicin itself was red, so the absorbance of PBS with different concentrations of the drug was used as background correction in the calculation. The mixture was mixed gently and incubated at 37° C. for 30 minutes. 80 μL of supernatant was obtained by centrifugation at 2000×g for 6 minutes, and the optical density of the supernatant at 541 nm was measured with a microplate reader (SpectraMax 190, Molecular Devices).

MTT experiment: HepG2 cells (a human liver cancer cell line commonly used to measure drug metabolism) were selected as the model cell line in this study. The cells were cultured in Dulbecco's modified Eagle's medium (DMEM) containing 10% fetal bovine serum (FBS; Gibco, Grand Island, NY, USA) and 1% 100×antibiotic-antimycotic (Gibco) at 37° C. under 5% $CO_2$. Cell viability was measured using a MTT cell proliferation detection kit (Cy-QUANT™; Invitrogen, Carlsbad, CA). Briefly, $2.0\times10^4$ cells/well of HepG2 cells were seeded and cultured in 96-well plates for 4 hours, and then 10 μL of 12-mM MTT stock solution and 100 μL of fresh DMEM medium were added to each well and cultured at 37° C. for 4 hours. Then 100 μL of SDS-HCl solution was added and incubated at 37° C. for 18 hours. The absorbance (A) value of each well was measured at 570 nm using a microplate reader (SpectraMax 190, Moleclar Devices).

In vivo method: To further evaluate the clinical potentials of different drug combinations, we performed biochemical assays and histological analyses to assess their toxicity in vivo. ICR mice were weighed and randomized into 2 groups, i.e., control groups and ZDV+RIF group. 100 mg/kg zidovudine and 80 mg/kg rifampicin were administered daily by gavage to the ZDV+RIF group for 1 week, while the control group was administered by gavage only normal saline. Each group consisted of 3 mice. Upon conclusion of the treatment, the mice were sacrificed and their blood, livers, and kidneys were collected. The evaluation of liver function was performed according to the following process. The blood samples were centrifuged for 5 minutes at 2000 rpm to obtain serum samples. The serum was tested for aspartate transferase (AST) activity. The AST content of the serum was determined using a detection kit (MAK055, Sigma Aldrich). The absorbance (A) value at 450 nm of each sample was measured by a microplate reader (SpectraMax 190, Molecular Devices). Elevation of AST (U/L) in serum represented an abnormality of the liver.

Histopathological analysis (HE staining) was performed according to the following process. Kidneys and livers were fixed with 10% formaldehyde solution overnight and then embedded in paraffin. The samples were then sent to the Veterinary Diagnostic Laboratory (VDL) of City University of Hong Kong for sectioning, stained with hematoxylin-eosin (H&E) and evaluated for histological characteristics.

The results from the above-described in vitro and in vivo toxicity tests showed that single and combinational uses of rifampicin and zidovudine led to low level of hemolysis and HepG2 cell lysis and no significant damage occurred in the liver and kidney was observed after 7 days, 10-fold therapeutic dose treatment (FIGS. 1F, 1G, 1H, 1I).

ITC Assay

Zidovudine is an HIV drug that inhibits the propagation of HIV virus through interfering with the activity of the viral reverse transcriptase. Studies have shown that the bacteriostatic effect of zidovudine may be that it interferes with the bacterial DNA replication process after phosphorylation. We hypothesized that the antibacterial effect of zidovudine may also be that it binds to the bacterial RNA polymerase complex as an uracil analog, thereby inhibiting the bacterial RNA transcription process. To test this hypothesis, we performed an ITC assay to test the direct binding of zidovudine to K. pneumoniae RNA polymerase. We successfully co-expressed the subunits of K. pneumoniae RNAp to prepare the required core enzyme by a dual plasmids expression system, pACYC-Duet and pET-Duet. The method is briefly described as follows:

Recombinant plasmids containing different subunits of RNAP (rpoA, rpoB, rpoC, rpoD, rpoZ) were constructed using the Gibson assembly method. First, all the required fragments were obtained by PCR amplification from the K. pneumoniae MGH78578 genome and two Duet plasmids, respectively. All fragments, Gibson Assembly Master Mix (NEB, #E2611S) and deionized water were then mixed and incubated at 50° C. for 60 minutes. The recombinant plasmids were transformed into E. coli DH5α by heat shock method. After verification via sequencing, the recombinant plasmids were then transformed into E. coli BL21(DE3). Plasmids pACYC Duet rpoA-rpoZ-Amp (encoding σ and ω subunits) and pET Duet rpoB-rpoC-Kana (encoding β and β' subunits) were transformed together into E. coli BL21 to prepare RNA core polymerase by in vivo assembly. The σ factor σ subunit was obtained by overexpression of E. coli BL21 containing the plasmid pET-Duet-rpoD-Kana alone. The recombinant bacteria were first cultured in LB agar containing 50 μg/mL of kanamycin and 100 μg/mL of ampicillin and then inoculated into LB broth containing same concentration of antibiotics at 37° C., 250 rpm. After the bacterial turbidity reached an OD600 of 0.6, 0.5 mM IPTG was added and cultured at 16° C., 200 rpm for 16 hours. Cells were harvested by centrifugation (5000 rpm, 20 minutes at 4° C.). The protein was then purified by affinity chromatography. To further obtain bacterial RNAp holoenzyme, RNAp core enzyme was incubated with sigma subunits at a molar ratio of 1:1 at 37° C. for 15 minutes and then used for subsequent ITC assays.

The interaction between RNAp and zidovudine was determined based on isothermal titration calorimetry (ITC) tests. To verify our hypothesis that zidovudine can inhibit the activity of bacterial RNA polymerases, the binding affinity of zidovudine to RNAp was verified by ITC measurement. The test was performed at 25° C. using a Malvern MicroCal PEAQ-ITC automatic ultrasensitive isothermal titration calorimeter (MicroCal (Malvern Instruments), Malvern, UK). RNA polymerase holoenzyme, bovine serum albumin (Sigma, USA) and zidovudine (Dalian Meilun Biotechnology Co., Ltd., Dalian, China) were prepared as a solution in 20:150 mM Tris-NaCl buffer (pH=7.9). 149.7 μM zidovudine was then dropped into the buffer containing 14.79 μM RNA polymerase and 15.05 μM BSA protein, respectively (molar ratio≈10:1); the procedure was: first injection of 0.5 μL, followed by 2 μL. The solution was stirred at 750 rpm. MicroCal PEAQ-ITC analysis software was used to fit the data to a one site binding model.

Figure 2:
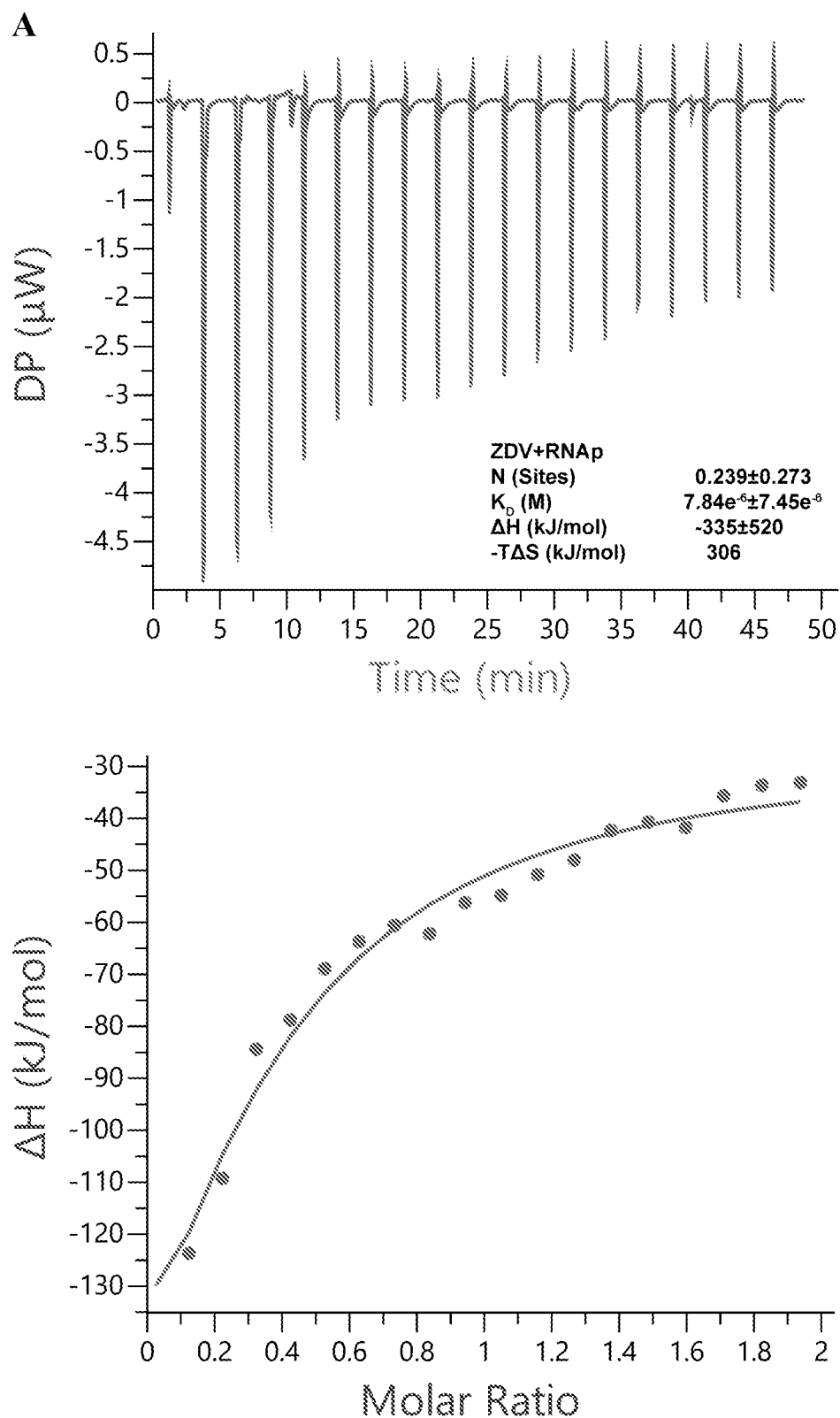
FIG. 2 depicts an analysis of the inhibition mechanism of ZDV and regulation of the virulence of CR-HvKP 1. (A) Representative isothermal titration calorimetry (ITC) traces and binding curve of titration between 149.7 μM zidovudine and 14.79 μM RNA polymerase (molar ratio≈10:1), (B) Representative isothermal titration calorimetry (ITC) traces and binding curve of titration between 149.7 μM zidovudine and 15.05 μM BSA protein (molar ratio≈10:1), (C) Predicted binding model of zidovudine with the β' subunit of *E. coli* RNAp which was analyzed by AutoDock Vina algorithm software and a binding model of rifampicin with the β subunit of RNAp (PDB: 5UAC), (D) String length (mm) for CR-HvKP 1 colonies at sheep blood agar containing different drugs, (E) $OD_{600}$ value represented mucoviscosity of CR-HvKP 1 bacterial culture solution under different drugs treatment, (F) Virulence gene rmpA2 expression under different drugs treatment. Data represents the mean±SD (n=3); statistical analysis was operated by one-way ANOVA for multiple groups. *P<0.05, P<0.01, *P<0.001.
Figure 2:
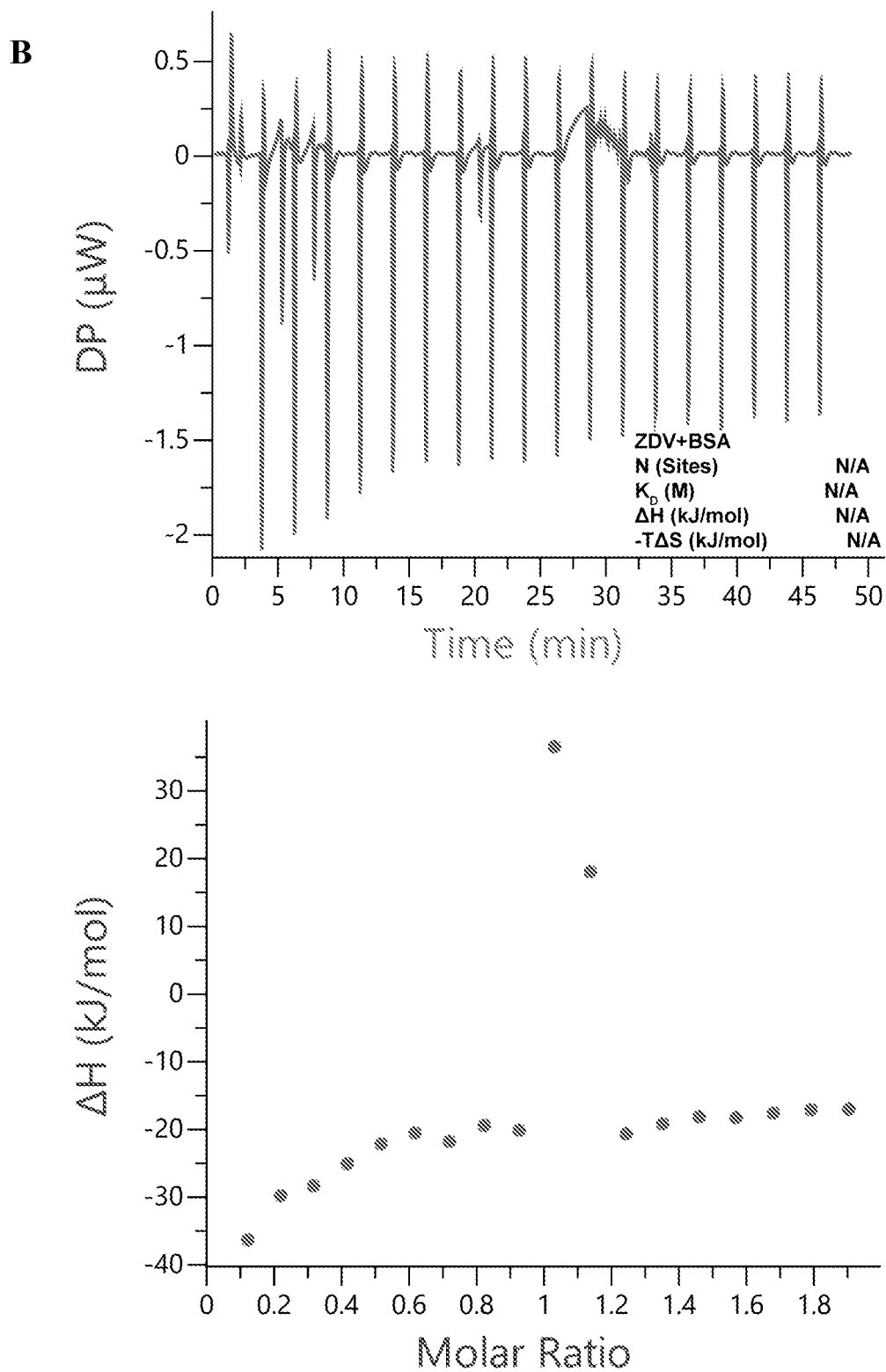
Figure 2:
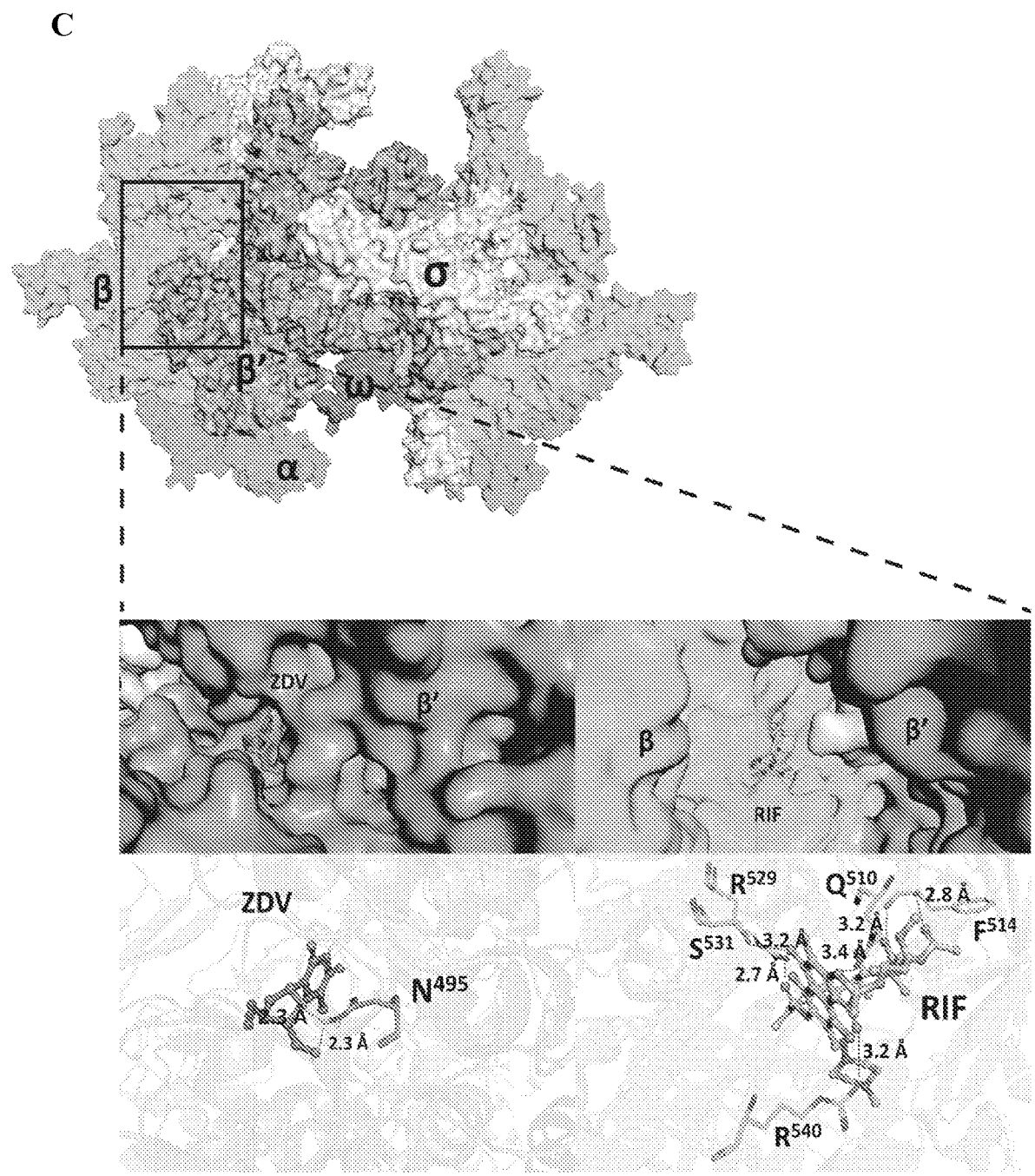
Figure 2:
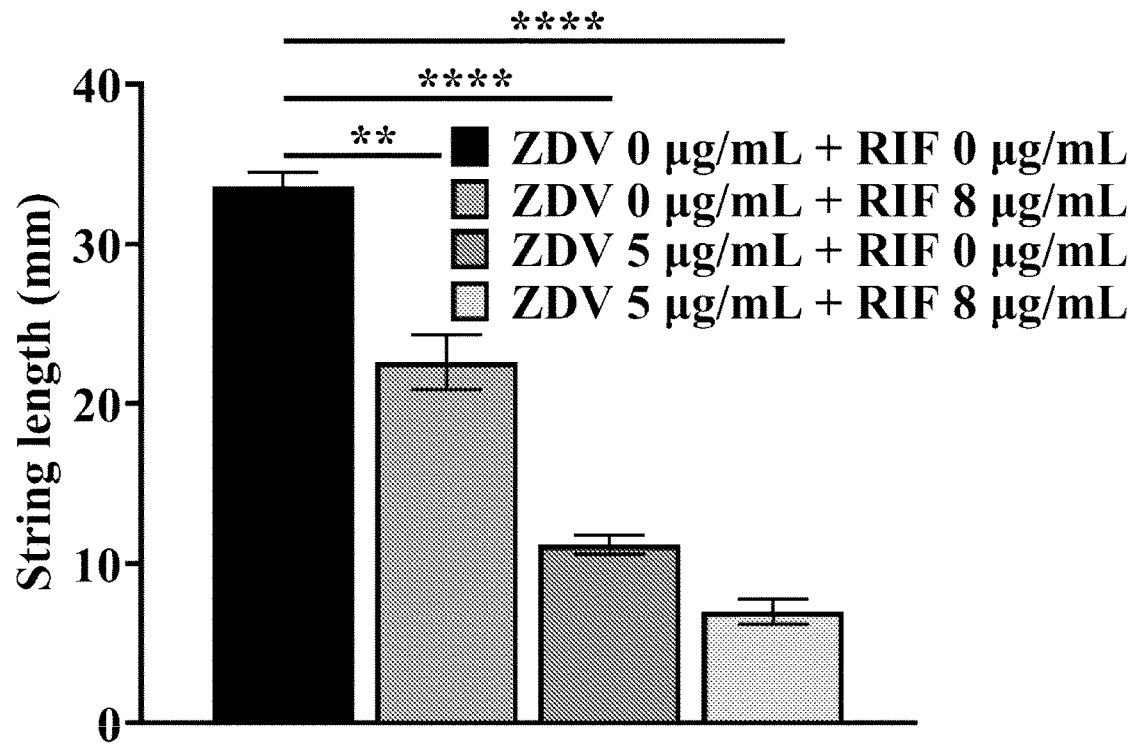
Figure 2:
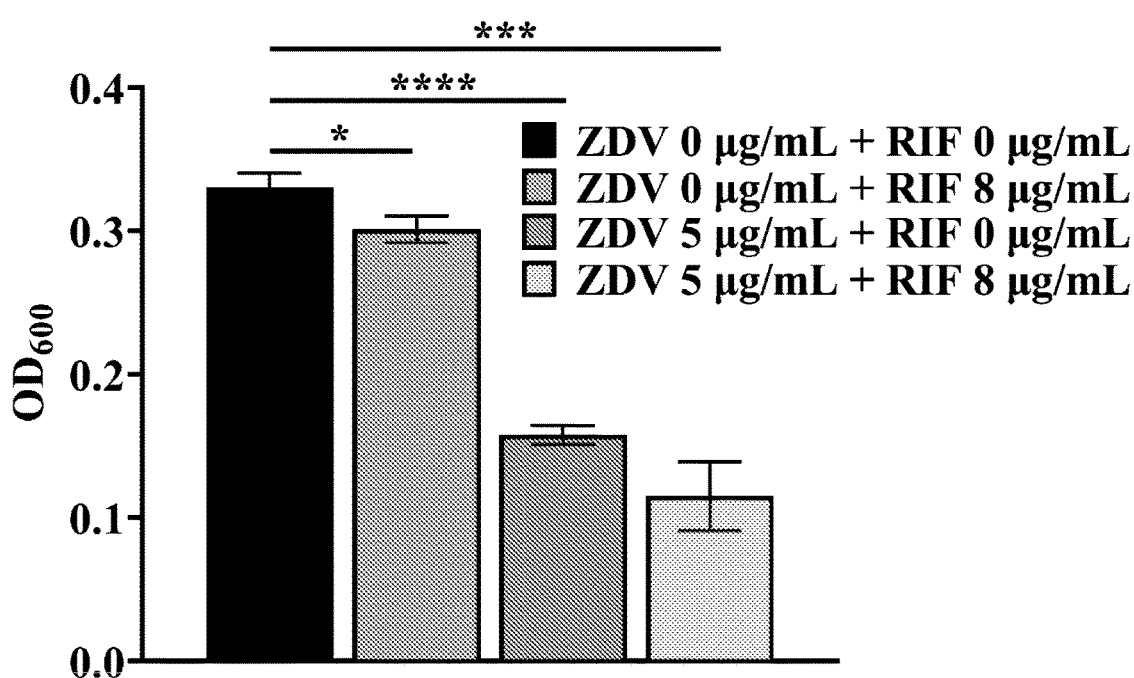
Figure 2:
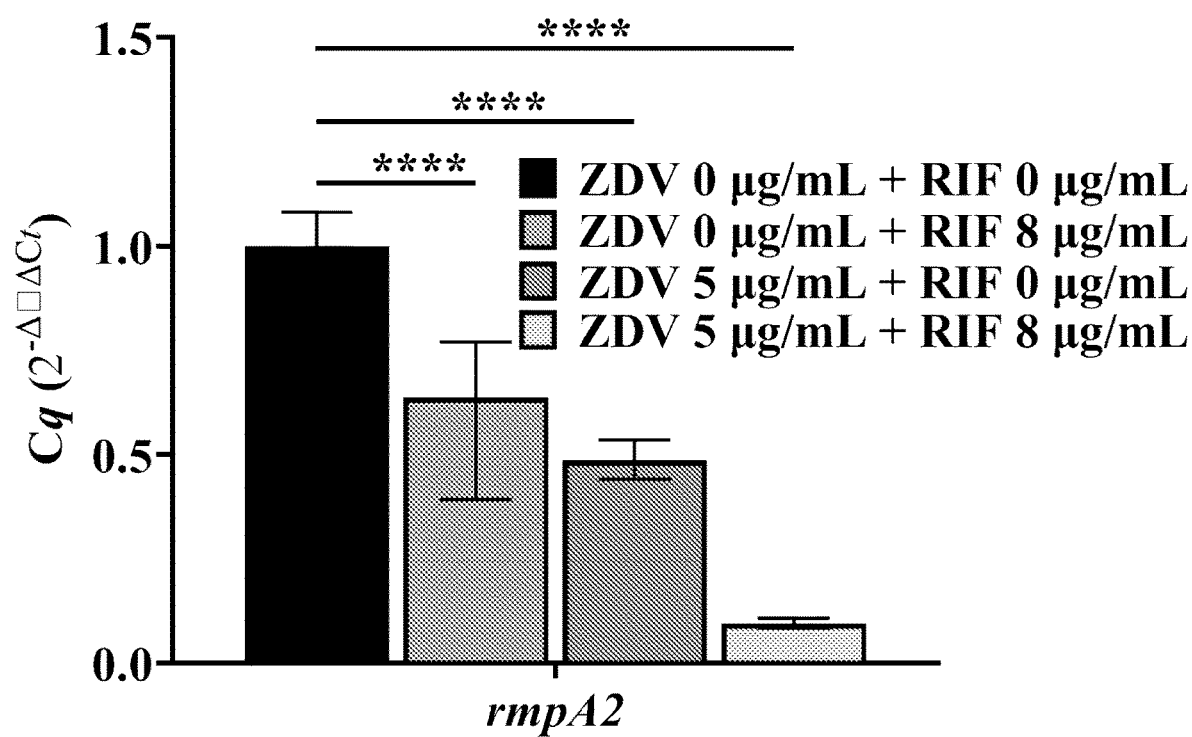

The results showed that $K_d$ of zidovudine was 7.8 μM, with the reaction stoichiometry (N sites) and enthalpy (ΔH) being 0.239±0.273 and −335±520 kJ/mol, respectively (FIGS. 2A, 2B). It implied that the small molecule of zidovudine had a high affinity to RNAp from the thermodynamic aspect. Molecular docking simulation of zidovudine to E. coli RNA polymerase (4YG2) was performed using AutoDock Vina. Zidovudine was shown to interact with the β' subunit of RNAp (encoded by the rpoC gene), which formed a tight contact (2.3 Å) with the residues Asn 495 in the chain J of the β' subunit, while rifampicin binds with theft subunit of RNAp (encoded by the rpoB gene) (FIG. 2C). Both binding pockets of rifampicin and zidovudine were located in the primary channel of RNAp near the active center. This observation suggests that zidovudine would inhibit bacterial growth through a mechanism similar to that of rifampicin but involves an alternative pathway.

It was last checked if inhibition of RNAp could inhibit the virulence expression of CR-HvKP. The method is briefly described as follows:

1. A series of tests were performed according to the following process. CR-HvKP 1 was inoculated onto the agar plate containing 5% sheep blood and different drugs and cultured overnight at 37° C. The series test refers to a test in which viscous strings greater than 5 mm in length are formed when a single colony is stretched with a standard bacteriological inoculating loop, which can be considered a virulent strain of a high-viscosity phenotype.

2. Mucoviscosity assay: The overnight culture of CR-HvKP 1 was re-inoculated into fresh LB broth to produce a bacterial broth with an $OD_{600}$ of 0.3. Different drugs were then added and cultured with shaking at 37° C. for 6 hours. The culture was then diluted to an $OD_{600}$ of 1.0 and centrifuged at 1,000×g for 2 minutes before the supernatant was obtained for $OD_{600}$ measurement.

The results of the data showed that rifampicin or zidovudine alone could reduce the string length and hypermucoviscosity (FIGS. 2D, 2E) as well as inhibition of the expression for a bacterial virulence factor rmpA2 by qRT-PCR (FIG. 2F).

In conclusion, this study has developed a pharmaceutical composition through drug repurposing approach for the treatment of infections caused by K. pneumoniae, especially CRKP and Carbapenem-resistant and hypervirulent K. pneumoniae (CR-HvKP) that exhibited a much higher mortality rate than CRKP.

What is claimed is:

1. A method of treating a Klebsiella pneumoniae infection in a subject in need thereof, the method consisting essentially of co-administering a therapeutically effective amount of rifampicin and zidovudine or pharmaceutically acceptable salts thereof to the subject.

2. The method of claim 1, wherein the Klebsiella pneumoniae infection is an antibiotic-resistant Klebsiella pneumoniae infection.

3. The method of claim 1, wherein the Klebsiella pneumoniae infection is a carbapenem-resistant K. pneumoniae (CRKP) infection.

4. The method of claim 1, wherein the Klebsiella pneumoniae infection is a carbapenem-resistant and hypervirulent K. pneumoniae (CR-HvKP) infection.

5. The method of claim 1, wherein rifampicin and zidovudine are each independently administered orally or by parentally.

6. The method of claim 1, wherein rifampicin and zidovudine are administered in the same pharmaceutical composition.

7. The method of claim 1, wherein rifampicin and zidovudine are administered in separate pharmaceutical compositions.

8. The method of claim 1, wherein rifampicin and zidovudine are co-administered at a mass ratio of 1:6-6:1.

9. The method of claim 1, wherein the subject is a human.

10. A method of disinfecting a surface, the method consisting essentially of: contacting the surface with rifampicin and zidovudine, wherein the surface is contaminated with Klebsiella pneumoniae or suspected of being contaminated with Klebsiella pneumoniae.

11. The method of claim 10, wherein the Klebsiella pneumoniae is antibiotic-resistant K. pneumoniae.

12. The method of claim 10, wherein the Klebsiella pneumoniae is carbapenem-resistant K. pneumoniae (CRKP).

13. The method of claim 10, wherein the Klebsiella pneumoniae is carbapenem-resistant and hypervirulent K. pneumoniae (CR-HvKP) infection.

* * * * *